US010660525B2

(12) United States Patent
Ladouceur et al.

(10) Patent No.: US 10,660,525 B2
(45) Date of Patent: May 26, 2020

(54) OPTRODE DEVICE

(71) Applicant: NEWSOUTH INNOVATIONS PTY LIMITED, Sydney (AU)

(72) Inventors: Francois Ladouceur, Waterloo (AU); Nigel Hamilton Lovell, Coogee (AU)

(73) Assignee: Newsouth Innovations PTY Ltd., Sydney (AU)

( * ) Notice: Subject to any disclaimer, the term of this patent is extended or adjusted under 35 U.S.C. 154(b) by 592 days.

(21) Appl. No.: 15/362,133

(22) Filed: Nov. 28, 2016

(65) Prior Publication Data

US 2017/0150889 A1 Jun. 1, 2017

(30) Foreign Application Priority Data

Nov. 27, 2015 (AU) .................................. 2015261698

(51) Int. Cl.
*A61B 5/00* (2006.01)
*A61B 5/04* (2006.01)
*A61B 5/0478* (2006.01)
*A61B 5/0492* (2006.01)

(52) U.S. Cl.
CPC ........ *A61B 5/0082* (2013.01); *A61B 5/04001* (2013.01); *A61B 5/0478* (2013.01); *A61B 5/0492* (2013.01); *A61B 2562/0209* (2013.01); *A61B 2562/0233* (2013.01); *A61B 2562/046* (2013.01); *A61B 2562/223* (2013.01)

(58) Field of Classification Search
CPC . A61B 5/0082; A61B 5/04001; A61B 5/0478; A61B 5/0492; A61B 2562/0209; A61B 2562/0233; A61B 2562/046; A61B 2562/223; G02F 2413/06
See application file for complete search history.

(56) References Cited

U.S. PATENT DOCUMENTS

2013/0144365 A1* 6/2013 Kipke ................ A61B 5/04001
607/93

FOREIGN PATENT DOCUMENTS

WO WO-2013110141 A1 * 8/2013 ............. G01R 29/12

* cited by examiner

*Primary Examiner* — Eun Hwa Kim
*Assistant Examiner* — James A Cipriano
(74) *Attorney, Agent, or Firm* — Hunton Andrews Kurth LLP

(57) ABSTRACT

The present disclosure provides a device for monitoring and visualising electrical activity of biological tissue. The device uses a sensor arrangement comprising a matrix of conductive sensors and a transducing element for transducing electric fields in a variation of an optical property. In use, electric fields generated by the biological tissue are sensed by the sensor arrangement and transduced by the transducing element for optical imaging.

22 Claims, 9 Drawing Sheets

OPTRODE DEVICE

FIELD OF THE INVENTION

The present invention relates to a device and a system for monitoring and visualising electrical activity of biological tissue.

BACKGROUND OF THE INVENTION

Monitoring and visualising electrical activity of biological tissue, such as neural, myocardial and other tissues, is of great importance in biomedicine.

Central nervous system (CNS) disorders in humans account for huge health care expenditures. The cost in Europe alone is estimated to be in the order of €800 billion annually. Deeper understanding of the underlying mechanisms governing neurophysiology and related neuropathologies is of great importance, and over the years many methods have been employed to gain a better understanding of the subtleties of these complex systems. Better understanding leads to higher diagnostic capabilities and thus opens avenues for therapeutic intervention with such disorders. Typical examples of such common ailments include epilepsy, Parkinson's disease, Alzheimer's and multiple sclerosis (MS).

In vivo and in vitro monitoring of bio-potentials is normally reliant on devices with classical electrodes. In these devices, each electrode needs to be individually connected by an electrical conductor to electronics for both the recording of information and also for stimulation. Due to the bulky nature of the wiring array and associated electronics, the number of interface channels is constrained to some tens or possibly hundreds.

There is a need in the art for improved and less invasive devices that can provide improved measurements of the electrical activity of biological tissue.

SUMMARY OF THE INVENTION

In accordance with a first aspect, the present invention provides a device for sensing electric fields generated by a biological tissue, the device comprising:
  a sensor arrangement arranged to sense electric fields;
  a transducing element arranged to transduce the electric field sensed by the plurality of sensitive regions into a variation of an optical property of a respective region of the transducing element;
  wherein in use electric fields generated by the biological tissue are sensed by the conductive sensor arrangement and transduced by the transducing element for optical imaging.

In an embodiment, the sensor arrangement further comprises a plurality of conductive regions and a reference electrode and each of the plurality of conductive regions comprises a sensing electrode that in use is biased, with respect to the reference electrode, with a voltage that is dependent on the magnitude of the electric field generated by the biological tissue in proximity of the conductive region.

The sensing electrodes may be separate from each other and disposed in an array of sensing electrodes across the device. In addition, they can be divided in groups of sensing electrodes with different dimensions. The surface area of the electrodes may be between $10^{-12}$ m$^2$ and $10^{-6}$ m$^2$.

Further, the sensing electrodes may be distributed on the device to provide a predetermined sensing pattern across a region of the biological tissue.

In embodiments, each sensing electrode comprises a high reflectivity portion arranged to reflect optical signals towards the reference electrode. The high reflectivity portion of the electrodes may be made of gold.

In embodiments, the device further comprises a polariser for filtering polarised light that filters light reflected from the sensing electrodes.

In embodiments, the reference electrode comprises a transparent portion extending across the device arranged to transmit optical signals towards the sensing electrode. The transparent portion may comprise a layer of indium thin oxide (ITO).

In embodiments, the transducing element comprises a layer of liquid crystals disposed between the sensing electrodes and the reference electrode. In these embodiments, the variation of the optical property of a region of the transducing element comprises a variation of birefringence of the liquid crystals at the region.

Advantageously, the liquid crystal layer may be arranged in a manner such that the optical property varies in a quantifiable manner with a variation of the sensed electric field. For example the birefringence may change substantially linearly with a variation of the sensed electric field down to the microvolt range.

In embodiments, the device further comprises a plurality of connections for connecting each sensing electrode to a respective conductive pad arranged to apply external electric signals to the electrode for tissue stimulation.

In embodiments, the sensing electrodes are formed onto a substrate, which may be flexible, and each of the plurality of connections arranged in a groove formed in the substrate.

In embodiments, the device is arranged in a manner such that the variation of the optical property of the transducing element can be imaged by a CCD camera or alternative imaging technology.

In embodiments, the device is arranged to be connected to one or more optical fibers or optical guides for propagating an optical light probe signal from a light source towards the device and an optical reflected signal from the device towards a light detector; the difference between the optical light probe signal and the optical reflected signal being a measure of the electric fields generated at one or more locations across the biological tissue.

In embodiments, the sensor arrangement comprises a plurality of separate sensing electrodes and each optical fiber is arranged to propagate the optical light probe signal towards a single sensing electrode and receive the optical reflected signal from the single sensing electrode after the reflected signal has been transmitted through the transducing element.

In embodiments, the device comprises a plurality of integrated beam splitters or blazed gratings for distributing the optical light probe signal from the one or more optical fibers or guides towards separate sensing electrodes and receiving the optical reflected signal from the respective sensing electrodes.

The sensor arrangement in the device may have a flexible structure and comprise biocompatible materials suitable for 'in vivo' operation.

In accordance with a second aspect, the present invention provides a device for sensing electric fields generated by a biological tissue, the device comprising:
  a semi-transparent reference electrode;

a plurality of sensing electrodes; each sensing electrode being arranged so that in use it develops a bias, with respect to the reference electrode, that is dependent on the magnitude of the electric field generated by the biological tissue in proximity of the sensing electrode; and a layer of liquid crystals arranged to transduce the electric field sensed by the plurality of sensitive regions into a variation of birefringence at a region of the layer.

In accordance with a third aspect, the present invention provides a system for monitoring the electrical activity of biological tissue, the system comprising:

a device for sensing electric fields generated by the biological tissue, the device comprising:
  a semi-transparent reference electrode;
  a plurality of sensing electrodes; each sensing electrode being arranged so that in use it develops a bias, with respect to the reference electrode, that is dependent on the magnitude of the electric field generated by the biological tissue in proximity of the sensing electrode;
  a layer of liquid crystals arranged to transduce the electric field sensed by the plurality of sensitive regions into a variation of birefringence at a region of the layer;

a light source and a light detector; and one or more optical fibers or optical guides arranged for propagating an optical light probe signal from the light source towards the device and an optical reflected signal from the device towards the light detector;

wherein in use electric fields generated by the biological tissue are sensed by the conductive sensor arrangement and transduced into a difference between the optical light probe signal and the optical reflected signal.

In accordance with a fourth aspect, the present invention provides a method for manufacturing a device for sensing electric fields generated by a biological tissue, the method comprising the steps of:

forming a plurality of conductive regions on a first substrate, the conductive regions being arranged as sensing electrodes;

forming a plurality of connections for connecting each conductive region to a peripheral region of the substrate;

forming a conductive electrode on a second substrate;

interconnecting the first and the second substrate in a manner such that a receptacle portion is formed between the first and the second substrate, the receptacle portion being arranged for receiving a layer of liquid crystals.

In embodiments, the step of forming a plurality of connections for connecting each conductive region to a peripheral region of the substrate comprises the steps of:

forming a plurality of grooves in the substrate using an etching technique; and depositing a conductive material into the grooves.

In accordance with a fifth aspect, the present invention provides a method for sensing electric fields generated by biological tissue, the method comprising the steps of:

sensing an electric field generated by the biological tissue;

converting the sensed electric field into a variation of an optical property; and providing an optical image.

An advantage of the device in accordance with embodiments is the capability to smoothly, continuously and passively transduce small electrical signals into the optical domain thus providing advantages typically associated with optical communications (parallelism, high-bandwidth).

Other advantages of embodiments of the device include providing analog transduction adapted to biological signals; high bandwidth real-time monitoring; fast sampling rates (>3 kHz per channel); no electrical connections required, no embedded power source required and linearity in absence of bias.

Advantageously the device and the system of the present invention may be used for both 'in vitro' and 'in vivo' applications. The nature of the device, with its lack of electrical wiring and circuitry facilitates use for in vivo applications, where space and electrode density is a crucial issue.

These advantages may provide improved capabilities for diagnosing and understanding the physiological mechanisms underlying biomedical and neurological conditions, in addition to gaining a deeper understanding of tissue models across a wide range of tissue types. This can lead to gaining new insights for a wide range of medical applications, such as restoring movement to paralysed patients, restoring sight to the vision impaired, stroke neuro-rehabilitation etc.

BRIEF DESCRIPTION OF THE DRAWINGS

Features and advantages of the present invention will become apparent from the following description of embodiments thereof, by way of example only, with reference to the accompanying drawings in which.

DETAILED DESCRIPTION OF SPECIFIC EMBODIMENTS

The embodiments are directed to a device and a system for monitoring and visualising electrical activity of biological tissue.

Embodiments of the device allow measuring small-signal voltages (down to the microvolt range) generated by biological tissue in a linear fashion with high modulation speed sufficient for AP (Amino-Pyridine) recording. The recording is made possible through a sensor arrangement comprising a plurality of conductive regions arranged to sense electric fields and a transducing element arranged to transduce the electric field sensed by the plurality of sensitive regions into a variation of an optical property of a respective region of the transducing element. The transducing element is provided in the form of a layer of DHFLC (Deformed Helix Ferroelectric Liquid Crystal) positioned between conducting electrodes. When the device is in use, electric fields generated by the biological tissue are sensed by the conductive sensor arrangement and transduced by the transducing element for optical imaging.

Figure 1B:
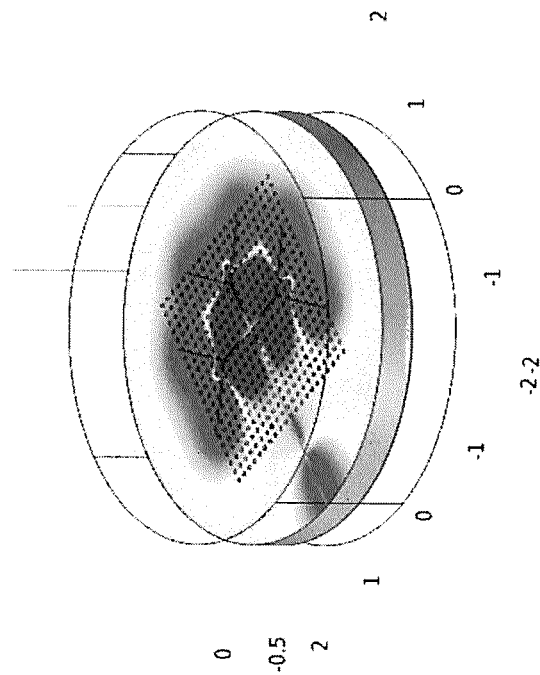
FIG. 1 shows illustrations of the device in accordance with embodiments.
Figure 1A:
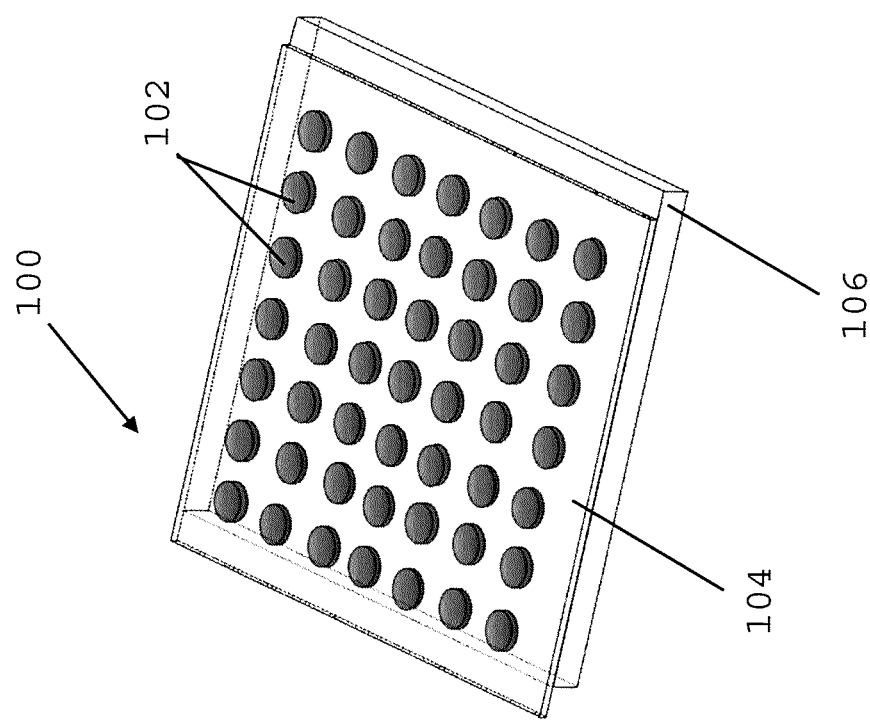

Referring now to FIG. 1, there are shown illustrations of the device in accordance with embodiments. FIG. 1(a) shows the front portion of a device 100 comprising a series of conductive sensing electrodes 102. The electrical activity of the biological tissue in proximity of each electrode creates a bias voltage between the sensing electrode and a reference electrode positioned on the other side of the device. The voltage is proportional to the magnitude of the electric field generated by the biological tissue.

Electrodes 102 are separate from each and realised in matrix arrangement on a polymer superstrate 104 for independently sensing an area of the tissue. They are realised in a semi-transparent substrate 106 which, in some cases is a flexible substrate.

FIG. 1(b) shows modelling results for device 100 when operating with a biological voltage input. Areas with different shading indicate modelled axons (neural tissue). Only the top portions of the device are shown in FIG. 1(a) and FIG. 1(b). For example, in FIG. 1(b) the device could be positioned in an in vitro environment and be covered with a saline solution while being imaged from underneath. The transducing layer of liquid crystals is not visible in the devices of FIG. 1.

Figure 2:
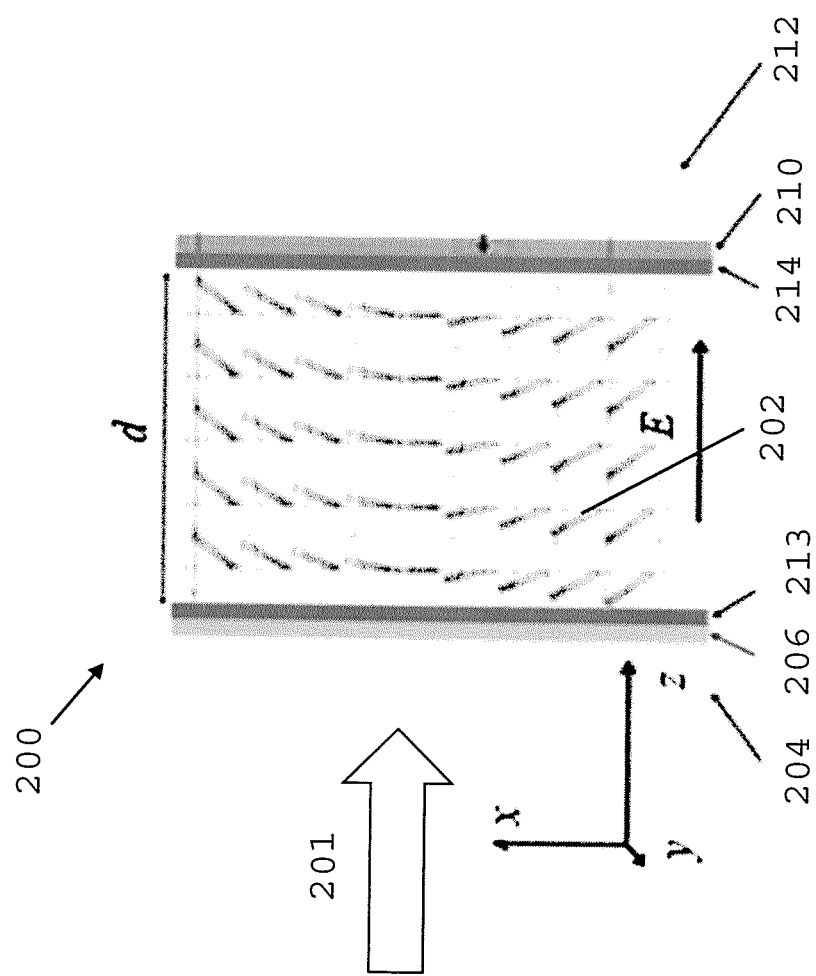
FIG. 2 shows a cross sectional view of a structure of a liquid crystal cell in accordance with embodiments.

Referring now to FIG. 2, there is shown a cross sectional view of a structure of a liquid crystal cell 200 in accordance with embodiments. The transducing layer of liquid crystals 202 is positioned in the centre of cell 200 in between the alignment layers 213 and 214 on either side. In the example of FIG. 2, light 201 enters the cell from the left side, through a glass layer 204. An ITO layer 206 is provided as a reference electrode. Light 201 is then incident upon the liquid crystals 202. Liquid crystals 202 rotate the angle of polarisation of the light to a degree relative to the voltage across ITO layer 206 and the respective sensing electrode, schematised in this figure as gold layer 210, which in this embodiment is used both as reflector and sensing electrode. The gold electrode is realised on a further glass substrate 212. The light is then reflected by a gold layer 210 and travels back towards liquid crystals 202. At this stage, a further rotation of the light occurs. Light 201 then goes through glass layer 204 and through a polariser (not shown in FIG. 2). The polariser thus acts as an analyser, allowing only the portion of light of the correct (original) polarisation to pass through. The light that goes through the polariser can be measured and is proportional to the electric field generated in proximity of the gold sensing electrode 210.

Figure 3:
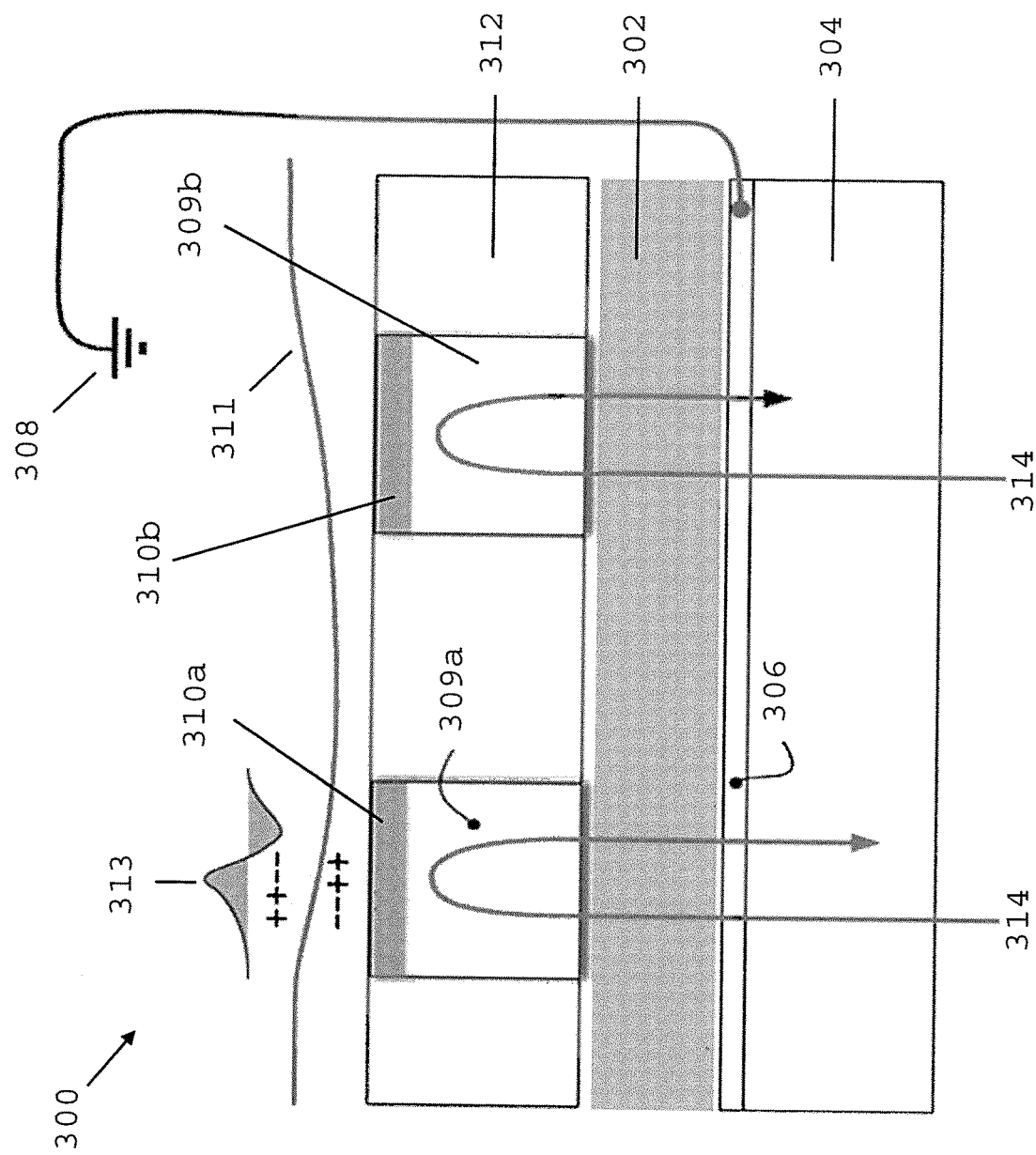
FIGS. 3 and 7 show schematic illustrations of a simplified devices in accordance with embodiments.

Referring now to FIG. 3 there is shown a schematic illustration of a simplified device 300 in accordance with embodiments. Device 300 comprises a liquid crystal cell as the one of FIG. 2 and two separate sensing electrodes 309a and 309b. Electrodes 309a and 309b comprise respective high reflectivity gold portions 310a and 310b. FIG. 3 shows two identical electrodes 309 for simplicity. Embodiments of the device disclosed herein have a plurality of electrodes disposed in a specific pattern to measure electrical activity across a surface of the biological tissue. In particular, the sensing electrodes can be organised in groups and have different dimensions. The surface area of the electrodes is comprised between $10^{-12}$ m$^2$ and $10^{-6}$ m$^2$. Electrodes 309 are positioned in proximity of excitable biological tissue 311. Activation in the biological tissue causes localised charges, illustrated as 313, in the extracellular potential. The charge creates a voltage between sensing electrodes 309 and reference electrode 306.

In FIG. 3, reference electrode 306 is provided as an ITO layer extending across the device and connected to ground 308. The reference electrode 306 is positioned on a transparent polymer substrate, whilst sensing electrodes 309 are realised in a polymer superstrate 312. The layer of liquid crystals 302 is positioned between the two polymeric layers.

Light 314 enters the device through the transparent polymer substrate 304 and passes through liquid crystals 302 before and after it is reflected by the gold portions 310a and 310b of the sensing electrodes. The birefringence of the liquid crystals 302 at the region in proximity of the biased electrodes varies in proportion to the biasing of the electrode and the electric field generated by the biological tissue. After exiting the device through substrate 304, light 314 has a different polarisation and is filtered using a polariser as described with reference to FIG. 2. One of the main advantages of this arrangement is that the variation of the reflected light is linear with the intensity of the electrical activity being monitored. The linearity of response is obtained by the precise selection of the angle between the polarizer's main axis and the liquid crystal's helical axis. This selection needs precise modelling of the device and needs to take into account the presence of multiple reflections within the cell. In practice, it is chosen experimentally by monitoring the device linearity during assembly.

Liquid crystals 302 are DHFLCs which provide low switching response time in the order of microseconds with a tuneable, threshold-free phase-shift, large birefringence and a low driving voltage. DHFLCs however are well suited to sensing applications as they display a fast response.

The DHFLCs are of a chiral smectic C* type. The LC molecules show a 'handedness' in orientation and the smectic type gives rise to a layered molecular structure, where the chiral rod-shaped molecules arrange themselves into horizontal smectic layers. Each layer contains molecules oriented in the same direction. This direction is dictated by an incremental rotation at a uniform tilt around a layer orthogonal 'director' as we progress through each layer. On a mesoscopic level, this gives rise to a helical structure as we progress through the smectic layers. The pitch length of the LC is defined as the physical length over which the layered molecules complete a full rotation.

The molecules of the liquid crystals are optically equivalent to a polarisation grating. Exposure to an electric field can change the direction of polarisation of the molecule and thus alter the birefringence of the liquid crystal. In this manner, applying a voltage across layer 302 can rotate the incident polarised light 314 in proportion to the strength of an applied voltage.

Figure 4:
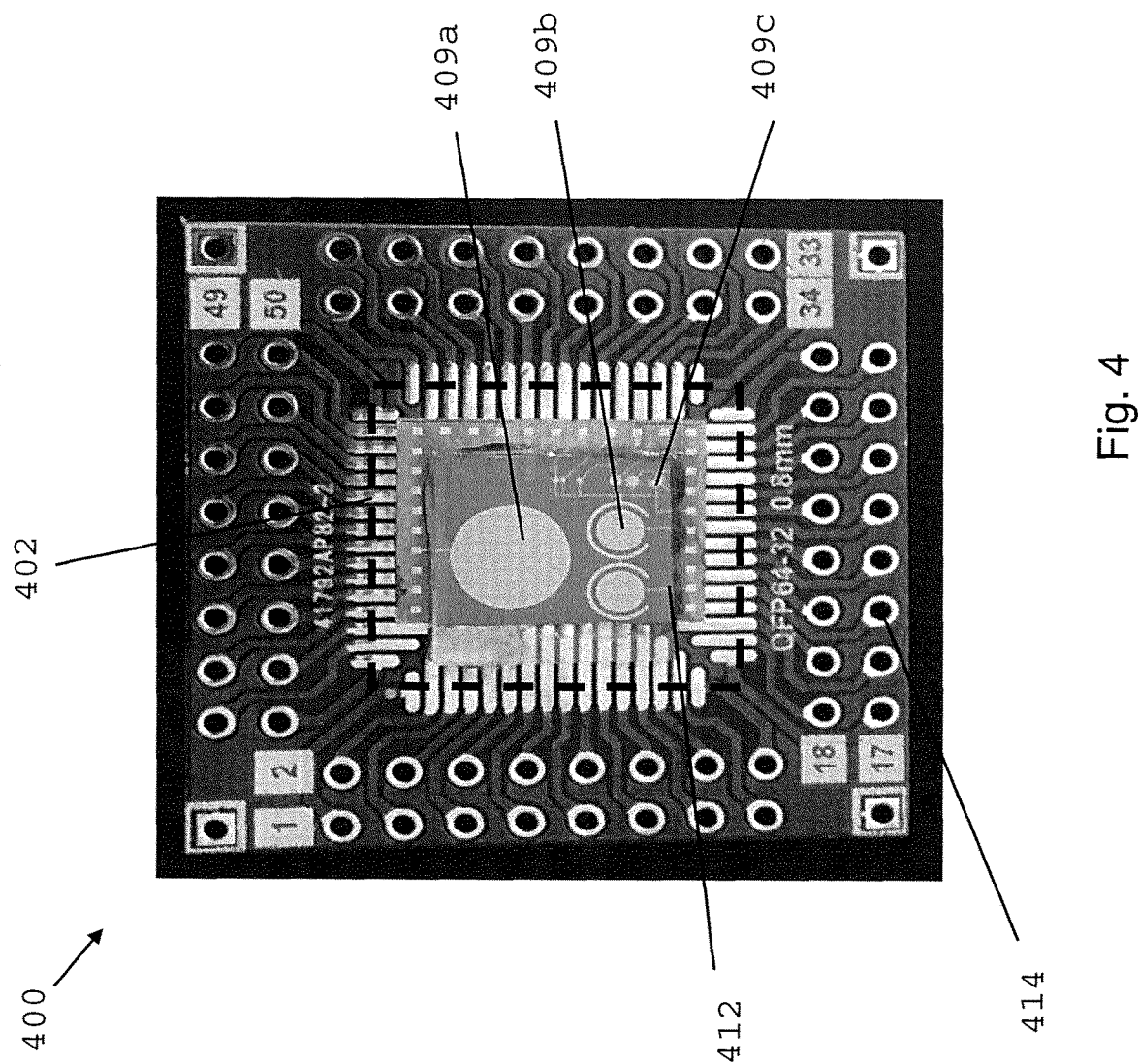
FIG. 4 is an illustration of a prototype device realised in accordance with embodiments.

Referring now to FIG. 4, there is shown an illustration of a prototype device 400 realised in accordance with embodiments realised by the applicants. In addition to measuring the electrical activity of the biological tissue, device 400 allows stimulating the tissue by applying electrical inputs to the electrodes.

Figure 5:
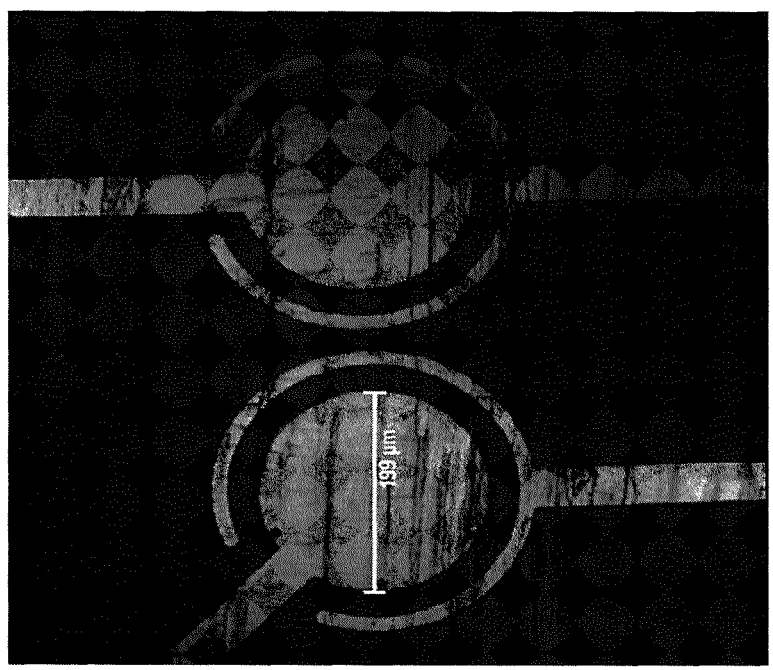
FIG. 5 is a microscopy image of a sensing electrode in accordance with embodiments.

The active portion 402 of device 400 (sensing) is positioned in the centre of the chip. Sensing electrodes of different shapes are formed on the glass substrate. Electrodes 409a have a diameter of 5 mm and no ground annuli, electrodes 409b have a diameter of 2 mm and also ground annuli, whilst electrodes 409c have a diameter of 0.5 mm. The electrodes are realised by patterning gold on one side of the liquid crystal cell. A magnified microscopy image of an electrode is shown in FIG. 5.

Each electrode 409 is electrically connected (see connection 412) to a peripheral contact on the chip through the substrate (see connection pad 414 at the periphery of the chip. This is achieved by creating holes in the substrate and using electroplating to fill them with an appropriate conductor (for example, gold).

The fabrication processes of device 400 involved standard micro fabrication techniques to first pattern the substrate and then deposit titanium and gold before lift-off thereby exposing the reflectors. Alignment layers were spun onto both the patterned substrate and an ITO coated glass substrate. The two substrates were brought together and glued to form a cell. The separation was ensured through the insertion of 5 μm diameter glass rods between the substrates. Finally, the cell was loaded with the LC. The new cell was mounted onto a generic chip holder and the electrical contacts bonded to the holder using an aluminium wedge bonder.

For in vitro use the device can be immersed in a saline bath with a biological sample in contact with the exposed electrical contacts. By applying small biological scale electrical stimulations by probe, the idea is to visualise the resulting bioelectrical response through imaging the device from underneath by microscope.

Figure 6:
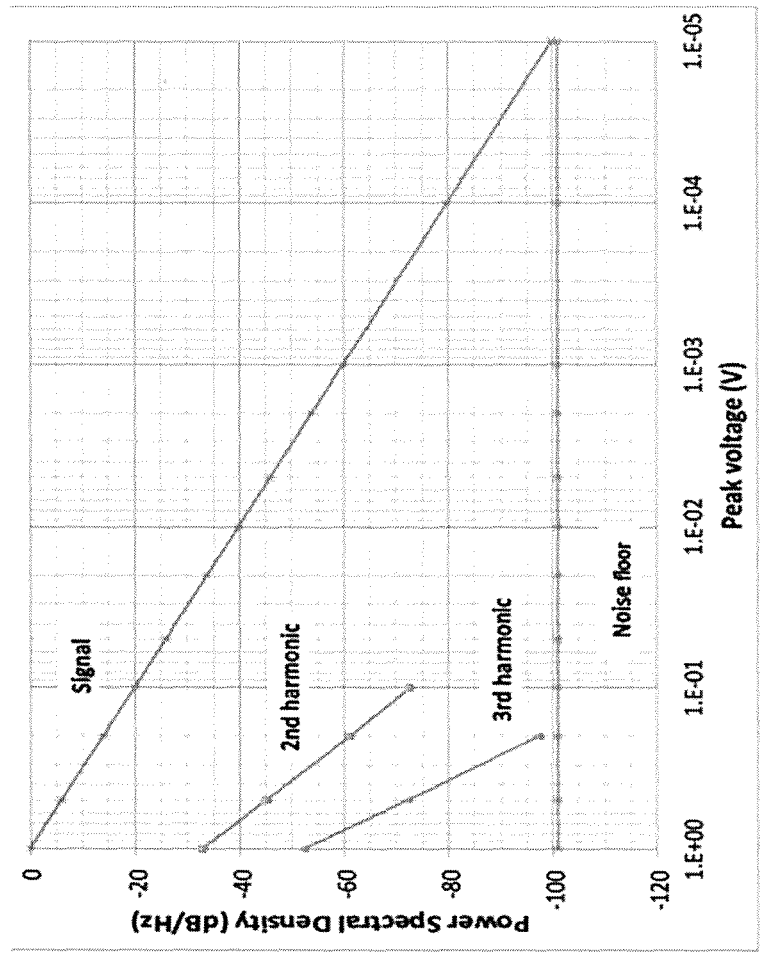
FIG. 6 shows data related to a response of a transducer in accordance with embodiment.

Referring now to FIG. 6, there are shown data related to a response of a transducer in accordance with embodiment. The response shows linearity over a dynamic range of 100 dB. The device performs the task passively, requiring no power and no electrical connectorisation. Biological signals thus acquired by the device can be imaged using a microscope and/or CCD (Charge Coupled Device) or a laser imaging device. In particular, the device can be arranged so that one or more optical fibers can be used to propagate an optical light probe signal from a light source towards the device and an optical reflected signal from the device towards a light detector. A single optical fiber can be used to propagate the optical light probe signal towards a single sensing electrode and receive the optical reflected signal from the single sensing electrode after the reflected signal has been transmitted through the transducing element.

Figure 7:
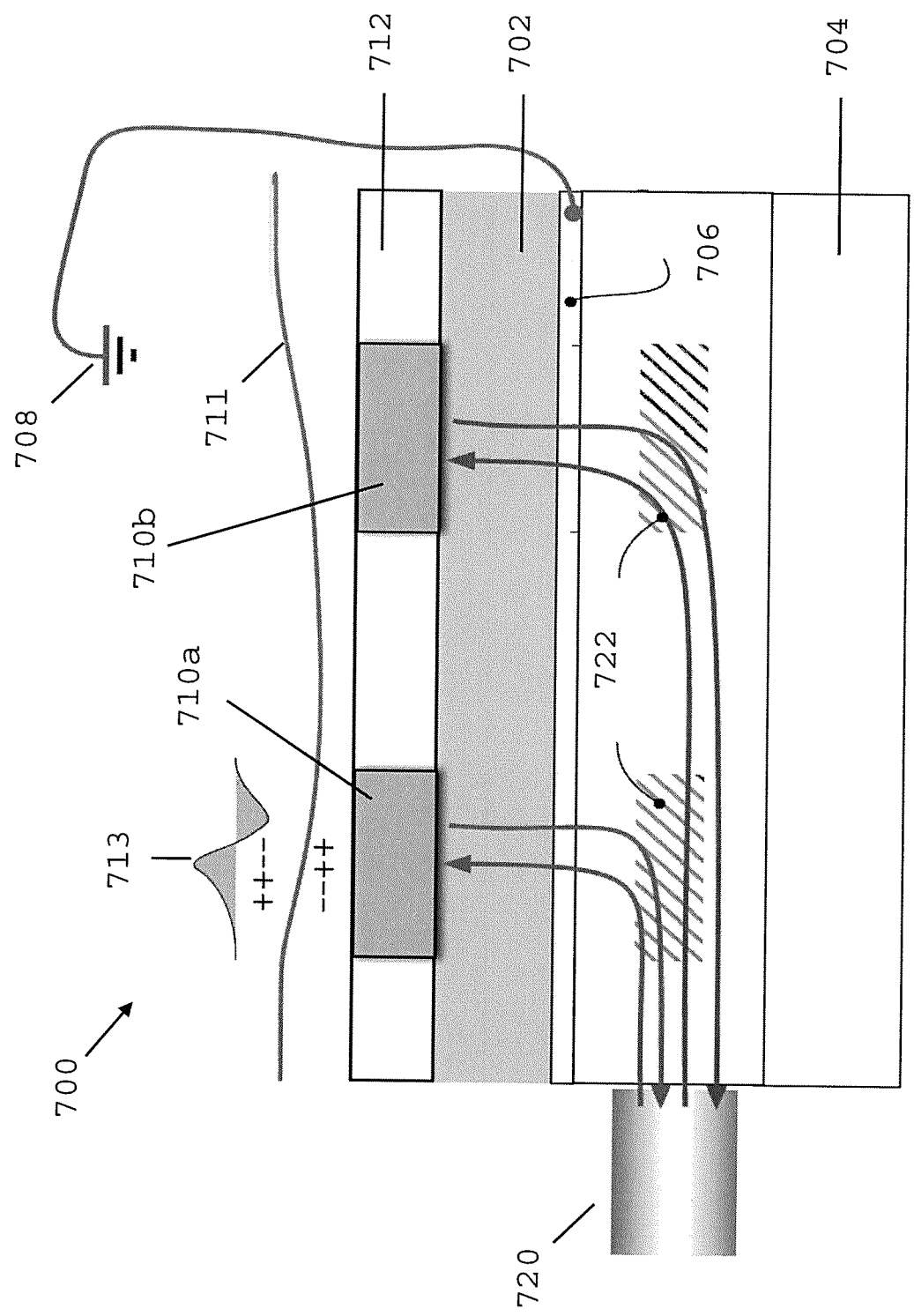

Referring now to FIG. 7, there is shown a further embodiment of the device 700 suitable for in vivo applications. The configuration of device 700 is similar to the device of FIG. 3. Device 700 comprises a transducing layer of liquid crystals 702, polymeric substrate and superstrate 704 and 712, sensing electrodes 710*a* and 710*b* for sensing the electrical activity of biological tissue 711. The ITO reference electrode 706 is electrically grounded to ground 708.

Device 700, however, is not imaged locally using a light from the bottom. Instead an optical fiber 720 is connected to a side of the device and a system of integrated blazed gratings 722 allows distributing the optical light probe signal from the optical fiber towards the reflective surfaces of electrodes 710. At the same time, optical fiber 720 allows receiving the optical reflected signal from the respective sensing electrodes 710.

Figure 8:
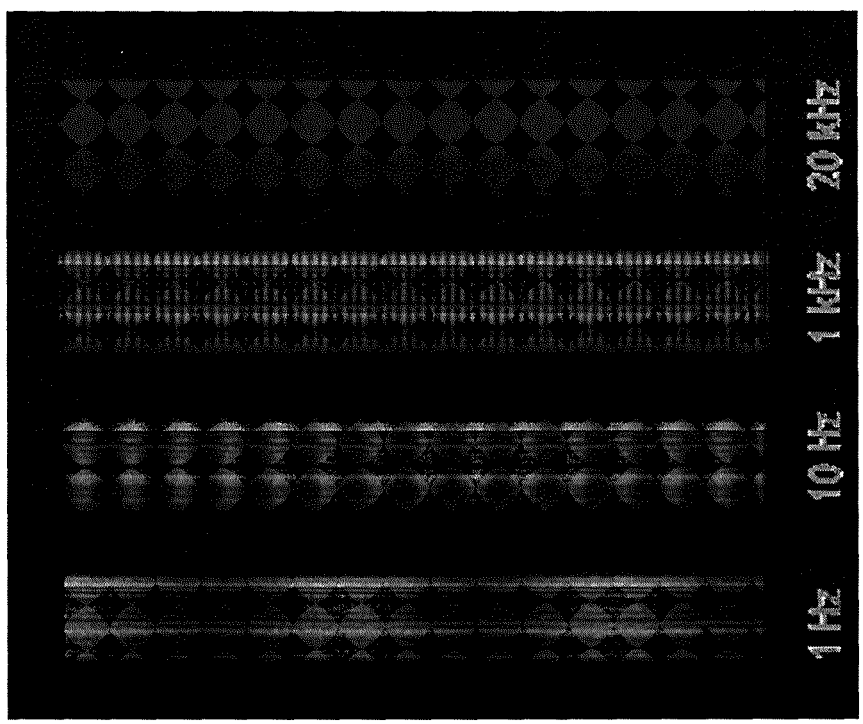
FIG. 8 shows a kymography dynamical response of a specific region of the device.

FIG. 8 shows a kymography dynamical response of a specific region of the device. The response of the individual electrodes was tested with 1550 nm light delivered to the cell by optical fiber (as in the standard transducer) and showed an optical response completely in line with expectations. Although this is not the regime under which the proposed device will operate, this does imply that the electrodes/mirrors in the device will affect the LC in a localised manner. This was accomplished with electrodes down to 200 μm in diameter; below this size it became difficult to focus the beam accurately onto the reflector with our setup.

Using a Leica TCS SP5 II confocal microscope, individual regions of interest (ROIs) were imaged using light at 670 nm. Kymographs of the ROIs could be produced as shown in FIG. 8. The dynamic response of the ROI can easily be visualised in the kymographs, where the x-axis corresponds to the spatial width of the ROI in the form of a line-scan, and the y-axis shows time. Dynamical response can also be directly plotted showing the magnitude of the said response. Using the microscope, we were able to see a clean response right down to the smallest electrodes (20 μm in diameter). Although the device behaved as expected and its dynamic response was clear, we noticed some cross talk between adjacent electrodes. We attempted to mitigate this issue through the addition of a grounded annulus surrounding some of the reflectors (this can be seen in FIG. 4).

Figure 9:
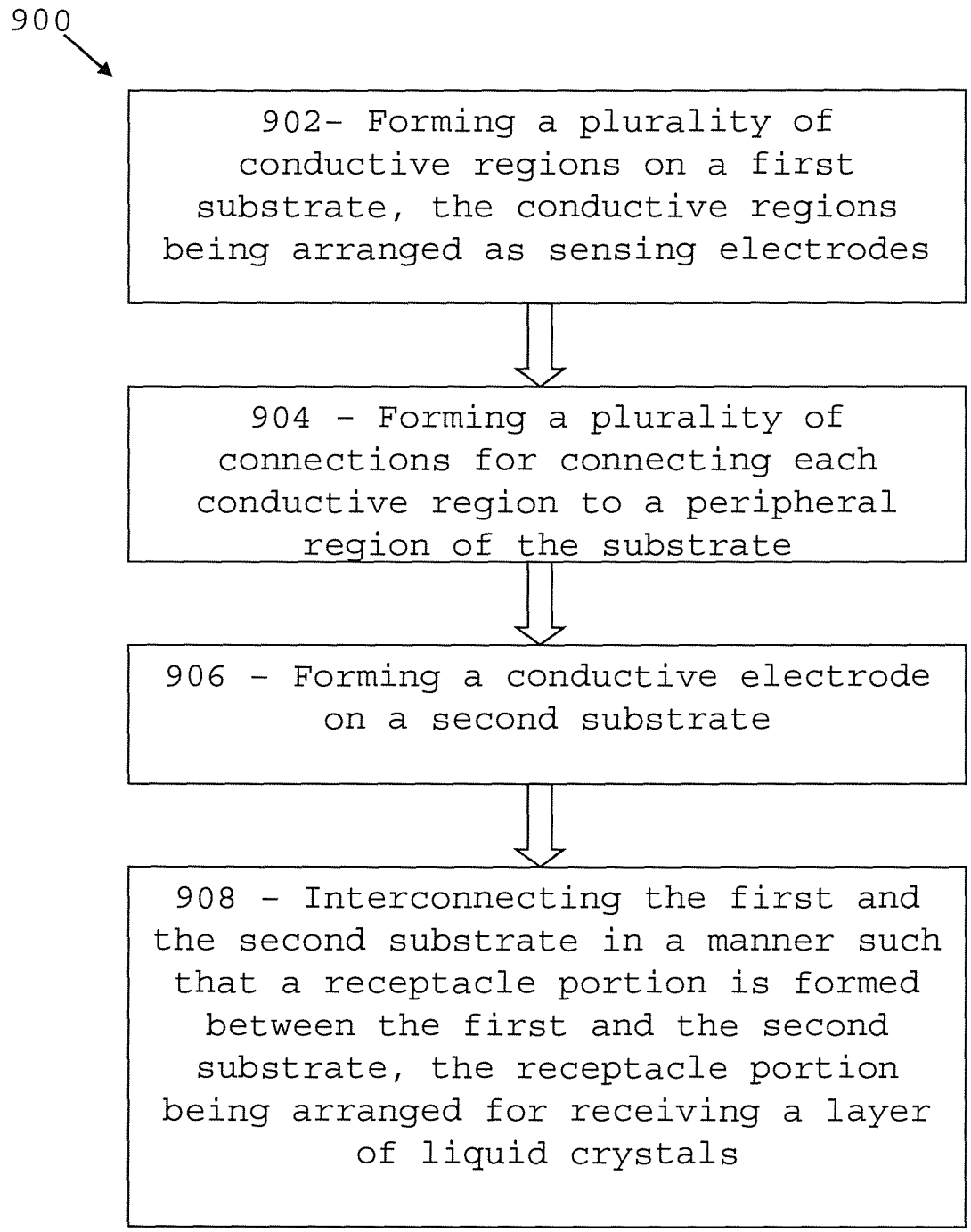
FIG. 9 is a flow-diagram of a method for manufacturing a device in accordance with embodiments.

Referring now to FIG. 9, there is shown a flow-diagram 900 outlining method steps for manufacturing a device in accordance with an embodiment. At step 902, a plurality of conductive regions is formed on a first substrate. These conductive regions will serve as sensing electrodes in the final device. Subsequently, or concurrently to forming the sensing regions, plurality of connections for connecting each conductive region to a peripheral region of the substrate is formed, step 904. These connections will allow electrical interconnection to the sensing electrodes to use them for stimulation. Subsequently a conductive electrode is formed on a second substrate, step 906. The first and the second substrate are interconnected at step 908 in a manner such that a receptacle portion is formed between the first and the second substrate, the receptacle portion is arranged for receiving a layer of liquid crystals. The layer of liquid crystals is then inserted in the receptacle portion.

As discussed above with reference to FIG. 4, step 904 can be performed by forming a plurality of grooves in the substrate using an etching technique and depositing a conductive material into the grooves. This is generally the same material used for the sensing electrodes.

Some of the illustrations and examples shown in this disclosure refer to devices with two electrodes. These illustrations have been used for simplicity of explanation only. The invention relates to devices comprising an array of sensing electrodes arranged to optimally measure the electrical activity of a biological tissue.

It will be appreciated by persons skilled in the art that numerous variations and/or modifications may be made to the invention as shown in the specific embodiments without departing from the spirit or scope of the invention as broadly described. The present embodiments are, therefore, to be considered in all respects as illustrative and not restrictive.

The term "comprising" (and its grammatical variations) as used herein are used in the inclusive sense of "having" or "including" and not in the sense of "consisting only of".

The invention claimed is:

1. A device for sensing electric fields generated by a biological tissue, the device comprising:
   a conductive sensor arrangement arranged to sense electric fields, the conductive sensor arrangement comprising a plurality of conductive regions each comprising a sensing electrode, and a reference electrode common to the plurality of conductive regions; and
   a transducing element arranged to transduce the electric field sensed by the plurality of conductive regions into a variation of an optical property of a respective region of the transducing element;
   wherein in use electric fields generated by the biological tissue are sensed by the conductive sensor arrangement and transduced by the transducing element for optical imaging.

2. The device of claim 1, wherein each sensing electrode in use is biased with respect to the reference electrode, with a voltage that is dependent on the magnitude of the electric field generated by the biological tissue in proximity of the conductive region.

3. The device of claim 2, wherein the sensing electrodes are separate from each other and disposed in an array of sensing electrodes across the device.

4. The device of claim 3, wherein the sensing electrodes are divided in groups of sensing electrodes with different dimensions.

5. The device of claim 4, wherein the surface area of the sensing electrodes is between $10^{-12}$ m$^2$ and $10^{-6}$ m$^2$.

6. The device of claim 3, wherein the sensing electrodes are distributed on the device to provide a predetermined sensing pattern across a region of the biological tissue.

7. The device of claim 3, wherein each of the sensing electrodes comprises a high reflectivity portion arranged to reflect optical signals towards the reference electrode.

8. The device of claim 7, wherein the device further comprises a polariser for filtering polarised light, the polariser being arranged in a manner such that, light reflected from the sensing electrodes is filtered by the polariser.

9. The device of claim 2, wherein the reference electrode comprises a transparent portion extending across the device arranged to transmit optical signals towards the sensing electrode.

10. The device of claim 2, wherein the transducing element comprises a layer of liquid crystals disposed between the sensing electrodes and the reference electrode.

11. The device of claim 10, wherein the variation of the optical property of a region of the transducing element comprises a variation of birefringence of the liquid crystals at the region.

12. The device of claim 10, wherein the liquid crystal layer is arranged in a manner such that the optical property varies in a quantifiable manner with a variation of the sensed electric field.

13. The device of claim 10, wherein the liquid crystal layer is arranged in a manner such that the optical property varies substantially linearly with a variation of the sensed electric field.

14. The device of claim 2, wherein the device further comprises a plurality of connections for connecting each sensing electrode to a respective conductive pad arranged to apply external electric signals to the sensing electrode for tissue stimulation.

15. The device of claim 14, wherein the sensing electrodes are formed onto a substrate and each of the plurality of connections is arranged in a groove formed in the substrate.

16. The device of claim 1, wherein the device is arranged in a manner such that the variation of the optical property of the transducing element can be imaged by a CCD camera or a laser imaging device.

17. The device of claim 1, wherein the device is arranged for connection to one or more optical fibers or optical guides arranged for propagating an optical light probe signal from a light source towards the device and an optical reflected signal from the device towards a light detector; the difference between the optical light probe signal and the optical reflected signal being a measure of the electric fields generated at one or more locations across the biological tissue.

18. The device of claim 17, wherein each of the one or more optical fibers or optical guides is arranged to propagate the optical light probe signal towards corresponding sensing electrode of the sensing electrodes and receive the optical reflected signal from the corresponding sensing electrode after the reflected signal has been transmitted through the transducing element.

19. The device of claim 17, wherein the device further comprises a plurality of integrated beam splitters or blazed gratings for distributing the optical light probe signal from the one or more optical fibers or guides towards separate sensing electrodes and receive the optical reflected signal from the separate sensing electrodes.

20. The device of claim 1, wherein the conductive sensor arrangement has a flexible structure and comprises biocompatible materials suitable for 'in vivo' operation.

21. A device for sensing electric fields generated by a biological tissue, the device comprising:
    a plurality of sensing electrodes;
    a semi-transparent reference electrode common to the plurality of sensing electrodes;
    wherein each of the plurality of sensing electrodes being arranged so that in use it develops a bias, with respect to the semi-transparent reference electrode, that is dependent on the magnitude of the electric field generated by the biological tissue in proximity of the sensing electrode; and
    a layer of liquid crystals arranged to transduce the electric field sensed by the plurality of sensitive regions into a variation of birefringence at a region of the layer.

22. A system for monitoring the electrical activity of biological tissue, the system comprising:
    a device for sensing electric fields generated by the biological tissue, the device comprising:
        a plurality of sensing electrodes;
        a semi-transparent reference electrode common to the plurality of sensing electrodes;
        wherein each sensing electrode being arranged so that in use it develops a bias, with respect to the reference electrode, that is dependent on the magnitude of the electric field generated by the biological tissue in proximity of the sensing electrode;
        a layer of liquid crystals arranged to transduce the electric field sensed by the plurality of sensing electrodes into a variation of birefringence at a region of the layer;
        a light source and a light detector; and
        one or more optical fibers or optical guides arranged for propagating an optical light probe signal from the light source towards the device and an optical reflected signal from the device towards the light detector;
    wherein in use, electric fields generated by the biological tissue are sensed by the plurality of sensing electrodes and transduced into a difference between the optical light probe signal and the optical reflected signal.

\* \* \* \* \*